(12) United States Patent
Hikosaka et al.

(10) Patent No.: US 6,817,360 B2
(45) Date of Patent: Nov. 16, 2004

(54) RESPIRATORY GAS SUPPLYING APPARATUS

(75) Inventors: Toru Hikosaka, Ibaraki (JP); Mamiko Mizuta, Ibaraki (JP); Shigenori Hirano, Ibaraki (JP); Katsuhiko Okada, Hino (JP); Mitsuru Uchiyama, Iwakuni (JP)

(73) Assignee: Teijin Limited, Osaka (JP)

( * ) Notice: Subject to any disclaimer, the term of this patent is extended or adjusted under 35 U.S.C. 154(b) by 133 days.

(21) Appl. No.: 09/979,801

(22) PCT Filed: Mar. 28, 2001

(86) PCT No.: PCT/JP01/02598

§ 371 (c)(1),
(2), (4) Date: Nov. 27, 2001

(87) PCT Pub. No.: WO01/72364

PCT Pub. Date: Oct. 4, 2001

(65) Prior Publication Data

US 2002/0157671 A1 Oct. 31, 2002

(30) Foreign Application Priority Data

Mar. 28, 2000 (JP) ........................................ 2000-088190
Dec. 25, 2000 (JP) ........................................ 2000-392305

(51) Int. Cl.[7] .............................................. A62B 9/04

(52) U.S. Cl. ........................... 128/202.27; 128/204.26; 128/206.27

(58) Field of Search ...................... 128/202.27, 204.26, 128/205.21, 205.22, 206.27, 204.18, 205.24, 205.25; 224/407, 576, 585; 280/35, 37, 47.26, 642; 312/123, 201, 298, 300, 321.5, 322; 248/122, 129

(56) References Cited

U.S. PATENT DOCUMENTS

| | | | | |
|---|---|---|---|---|
| 492,878 A | * | 3/1893 | Siebel | 312/270.2 |
| 1,244,030 A | * | 10/1917 | Cave | 239/71 |
| 1,374,986 A | * | 4/1921 | Carter | 414/426 |
| 1,793,637 A | * | 2/1931 | Rockwell | 280/47.26 |
| 2,042,474 A | * | 6/1936 | McKesson | 128/204.18 |
| 2,122,897 A | * | 7/1938 | Straw | 128/204.18 |
| 2,162,242 A | * | 6/1939 | Branower | 128/204.18 |
| 2,385,786 A | * | 10/1945 | Brubach et al. | 128/204.18 |
| 2,539,615 A | * | 1/1951 | Fox et al. | 222/135 |
| 2,577,290 A | * | 12/1951 | Underwood | 280/646 |
| 2,667,397 A | * | 1/1954 | Hallisey | 128/204.18 |
| 2,693,178 A | * | 11/1954 | Gilroy | 128/204.18 |
| 2,766,752 A | * | 10/1956 | Meidenbaur, Jr. | 128/204.18 |
| 2,881,757 A | * | 4/1959 | Haverland | 128/204.18 |
| 3,073,301 A | * | 1/1963 | Hay et al. | 128/205.24 |
| 3,136,442 A | * | 6/1964 | Massey | 220/3.8 |
| 4,243,155 A | * | 1/1981 | Stewart | 222/3 |
| 4,253,716 A | * | 3/1981 | Turner, Jr. | 312/100 |
| 4,383,528 A | * | 5/1983 | Eppolito | 128/205.22 |
| 4,438,764 A | * | 3/1984 | Eppolito | 128/205.22 |

(List continued on next page.)

Primary Examiner—Aaron J. Lewis
(74) Attorney, Agent, or Firm—Rader, Fishman & Grauer PLLC

(57) ABSTRACT

The invention provides an apparatus for supplying a respiratory gas to a respiratory air way of a patient. The respiratory gas supplying apparatus 10 includes a cylinder 12 filled with a respiratory gas, a cart 14 having an accommodating portion for disposing the cylinder 12, a shut-off valve 18 attached to the cylinder 12, a flow regulating valve 40 attached to the shut-off valve 18, a conduit 22, attached to the flow regulating valve 40, for directing the respiratory gas to the inlet of the respiratory airway of the patient, a coupler 16, integrally connected to the flow regulator 40, for coupling the flow regulating valve 40 to the shut-off is valve 18, and a linkage 110 for disengaging the coupler 16 from the shut-off valve IS when the cylinder 12 is detached from the cart 14.

16 Claims, 12 Drawing Sheets

U.S. PATENT DOCUMENTS

| | | | | |
|---|---|---|---|---|
| 4,469,097 A | * | 9/1984 | Kelman | 128/205.22 |
| 4,621,633 A | * | 11/1986 | Bowles et al. | 128/203.17 |
| 4,696,420 A | * | 9/1987 | Kulik | 224/275 |
| 4,861,059 A | * | 8/1989 | Shirk | 280/304.1 |
| 4,944,292 A | * | 7/1990 | Gaeke et al. | 128/204.18 |
| 4,960,120 A | * | 10/1990 | Constance-Hughes | 128/205.22 |
| 4,996,982 A | * | 3/1991 | Williamson | 128/205.24 |
| 5,052,400 A | * | 10/1991 | Dietz | 128/204.18 |
| 5,071,148 A | * | 12/1991 | Salvucci, Sr. | 280/47.24 |
| 5,131,670 A | * | 7/1992 | Clements et al. | 280/35 |
| 5,288,001 A | * | 2/1994 | Locarno | 224/407 |
| 5,335,651 A | * | 8/1994 | Foster et al. | 128/202.13 |
| 5,340,140 A | * | 8/1994 | Bynum | 280/304.1 |
| 5,370,111 A | * | 12/1994 | Reeder et al. | 128/202.13 |
| 5,386,824 A | * | 2/1995 | Nelepka | 128/204.18 |
| 5,396,885 A | * | 3/1995 | Nelson | 128/204.18 |
| 5,497,766 A | * | 3/1996 | Foster et al. | 128/200.24 |
| 5,613,490 A | * | 3/1997 | Mayes et al. | 128/205.22 |
| 5,655,524 A | * | 8/1997 | Atkins | 128/205.24 |
| 5,685,297 A | * | 11/1997 | Schuler | 128/205.24 |
| 5,887,585 A | * | 3/1999 | Dusenbery | 128/202.14 |
| 5,937,854 A | * | 8/1999 | Stenzler | 128/204.23 |
| 6,334,622 B1 | * | 1/2002 | Romero | 280/47.26 |
| 6,394,088 B1 | * | 5/2002 | Frye et al. | 128/204.26 |
| 6,427,690 B1 | * | 8/2002 | McCombs et al. | 128/204.26 |
| 6,484,721 B1 | * | 11/2002 | Bliss | 128/205.24 |
| 6,672,321 B2 | * | 1/2004 | Hamilton | 135/67 |

\* cited by examiner

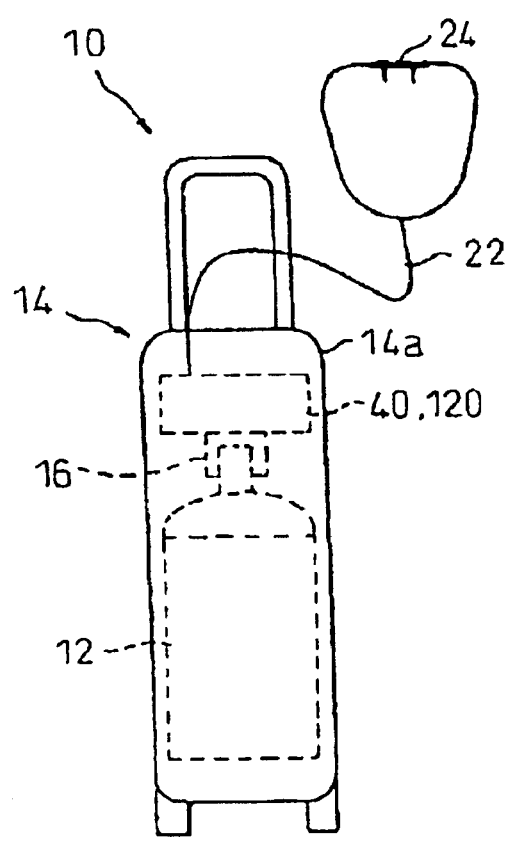
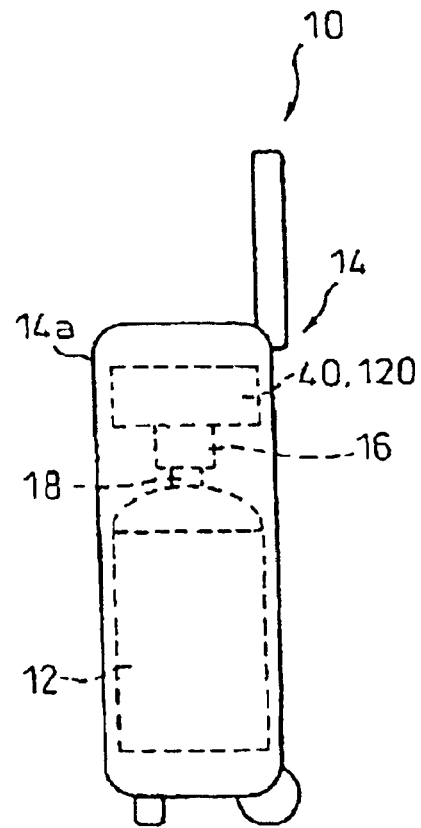

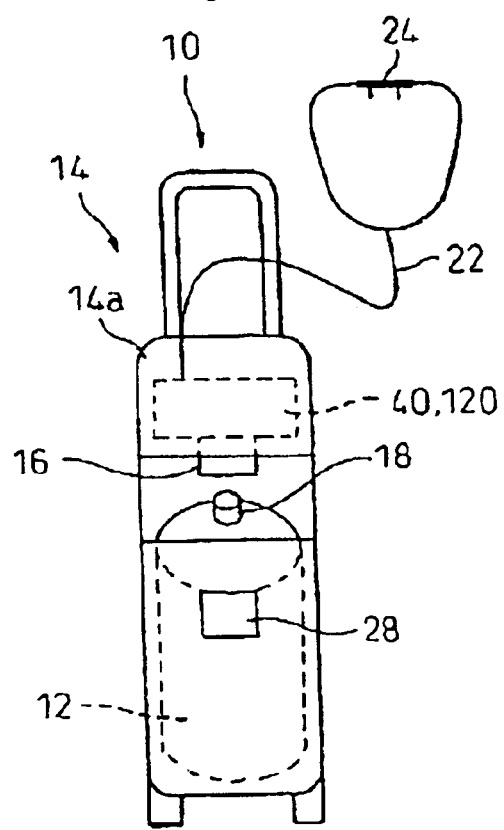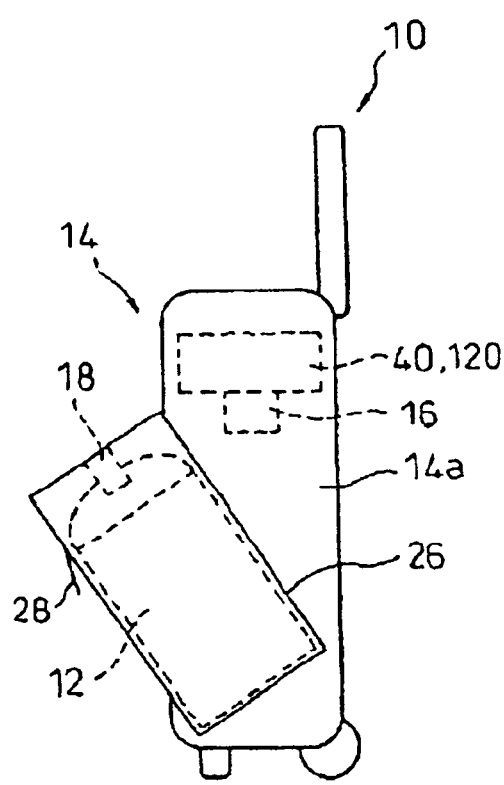

RESPIRATORY GAS SUPPLYING APPARATUS

TECHNICAL FIELD

The invention relates to an apparatus for supplying a respiratory gas to a user or a patient having a respiratory system disease.

BACKGROUND ART

In treatments for respiratory system diseases such as pulmonary emphysema or chronic bronchitis, oxygen inhalation is known as one of the most effective treatments. In oxygen inhalation therapy, oxygen gas or oxygen enhanced gas is supplied as a respiratory gas to the user from respiratory gas source such as an oxygen cylinder through a nasal cannula. Relatively large oxygen cylinders are used as respiratory gas source in hospitals or in the houses of the patients. On she other hand, when the patient goes out of his or her house, a compact portable oxygen cylinder is used. High pressure respiratory gas, compressed to about 20 Mpa, is filled in the portable oxygen cylinder because of its small volume.

FIG. 17 is a schematic diagram of a respiratory gas supplying apparatus including a conventional portable oxygen cylinder. In FIG. 17, a shut-off valve 2 is mounted to an oxygen cylinder 1. A flow regulating valve 3 is connected to the shut-off valve 2. A demand regulator 5 is connected to the flow regulating valve 3 through a conduit 4. From the demand regulator 5, respiratory gas is supplied to a user through a nasal cannula 7. The prior art shown in FIG. 17 is an example which includes a shut-off valve and a flow regulating valve according to the CGA (Compressed Gas Association) 670 and the flow regulating valve 3 is clamped to the housing of the shut-off valve 2 by a clamp bolt (not shown) connected to a handle 3a.

When the respiratory gas is consumed and pressure in the oxygen cylinder is reduced to a predetermined pressure level, this oxygen cylinder is replaced with a new one. At that time, the clamp bolt is loosened with the handle 3a rotated to remove the flow regulating valve 3 from the shut-off valve 2 on the oxygen cylinder 1. This work is bothersome to a user having a respiratory system disease.

The invention is directed to solve the above described problems of the prior art, and to provide a respiratory gas supplying apparatus which is improved to facilitate the replacement of the oxygen cylinder.

Further, the objective of the invention is to h provide a respiratory gas supplying apparatus which is improved to facilitate the attachment and detachment of the demand regulator to and from the oxygen cylinder.

DISCLOSURE OF THE INVENTION

According to the invention, there is provided an apparatus for supplying a respiratory gas to a respiratory airway of a patient. The apparatus includes a cylinder filled with a respiratory gas, a cart having an accommodating portion for disposing the cylinder, a shut-off valve attached to the cylinder, a flow regulating valve adapted to be attached to the shut-off valve, a conduit, attached to the flow regulating valve, for directing the respiratory gas to the respiratory airway of the patient, a coupler, integrally connected to the flow regulating valve, for coupling the flow regulating valve to the shut-off valve, and a linkage mechanism for disconnecting the coupler from the shut-off valve when the cylinder is detached from the cart.

Preferably, the accommodating portion includes a housing which can incline relative to the frame of the cart, a handle, rotatably secured to a wall Of the housing, for moving the housing relative to the frame of the cart, and the linkage mechanism is connected to the handle.

The flow regulating valve preferably has an inlet port for receiving the respiratory gas and an outlet port for discharging the respiratory gas to the conduit. The shut-off valve has a coupler mounting portion in the form of a column to which the coupler is mounted. The coupler mounting portion includes a peripheral groove extending along the outer surface and an outlet port which is adapted to be fluidly connected to the inlet port of the flow regulating valve when the coupler is mounted to the coupler mounting portion. The coupler includes an engaging claw which is adapted to engage the peripheral groove when the coupler is mounted to the coupler mounting portion and a releasing mechanism for disengaging the engaging claw from the peripheral groove when the coupler is detached from the coupler mounting portion. The linkage mechanism engages the releasing mechanism when the cylinder is mounted to the cart.

According to another feature of the invention, an apparatus for supplying a respiratory gas to a respiratory airway of a patient includes a cylinder filled with a respiratory gas, a cart having an accommodating portion for disposing the cylinder, a shut-off valve attached to the cylinder, a demand regulator adapted to be attached to the shut-off valve, a conduit, attached to the demand regulator, for directing the respiratory gas to the respiratory airway of the patient, a coupler, integrally connected to the demand regulator, for coupling the demand regulator to the shut-off valve, and a linkage mechanism for disconnecting the coupler from the shut-off valve when the cylinder is detached from the cart.

The demand regulator preferably has an inlet port for receiving the respiratory gas and an outlet port for discharging the respiratory gas to the conduit. The shut-off valve has a coupler mounting portion in the form of a column to which the coupler is mounted, the coupler mounting portion includes a peripheral groove extending along the outer surface and an outlet port which is adapted to be fluidly connected to the inlet port of the demand regulator when the coupler is mounted to the coupler mounting portion. The coupler includes an engaging claw which is adapted to engage the peripheral groove when the coupler is mounted to the coupler mounting portion and a releasing mechanism for disengaging the engaging claw from the peripheral groove when the coupler is detached from the coupler mounting portion. The Linkage mechanism engages the releasing mechanism when the cylinder is mounted to the cart.

The demand regulator may comprise a passage extending between the inlet port and the outlet port, pressure regulating means provided in the passage, a flow regulating means provided downstream of the pressure regulating means and a supply controlling unit, provided downstream of the flow regulating means, for fluidly connecting the outlet port to the inlet port when the patient is in the inspiration phase to supply the respiratory gas to the patient.

The supply controlling unit preferably comprises an inspiration sensor for detecting inspirations of the patient, a solenoid operated valve for fluidly connecting and disconnecting the inlet port and the outlet port and a solenoid driver circuit for opening the solenoid operated valve when the inspiration sensor detects the inspiration of the user.

An electric power source device for driving the solenoid of the solenoid operated valve may be provided in the respiratory gas supplying apparatus and the demand regulator may further comprise a pressure sensor for detecting the pressure in the passage. In this case, the demand regulator activates the electric cower source when the pressure in the passage increases to a predetermined high level and deactivates the electric power source device when the pressure in the passage decrease to the predetermined low level.

The shut-off valve attach to the cylinder may comprise a solenoid operated valve. The demand regulator may comprises a solenoid driver circuit for driving the solenoid of the solenoid operated driver, an electric power source device and a switch for opening and closing the shut-off valve through the solenoid driver circuit.

BRIEF DESCRIPTION OF THE DRAWINGS

FIG. 11A is a front view of an embodiment of a respiratory gas supplying apparatus according to the invention;

FIG. 11B is a side view of the respiratory gas supplying apparatus of FIG. 11A;

FIG. 12A is a front view of the respiratory gas supplying apparatus FIG. 11A in which a accommodating portion is forwardly pulled for the replacement of the oxygen cylinder;

FIG. 12B is a side view of the respiratory gas supplying apparatus of FIG. 12A;

BEST MODE FOR CARRYING OUT THE INVENTION

Figure 1:
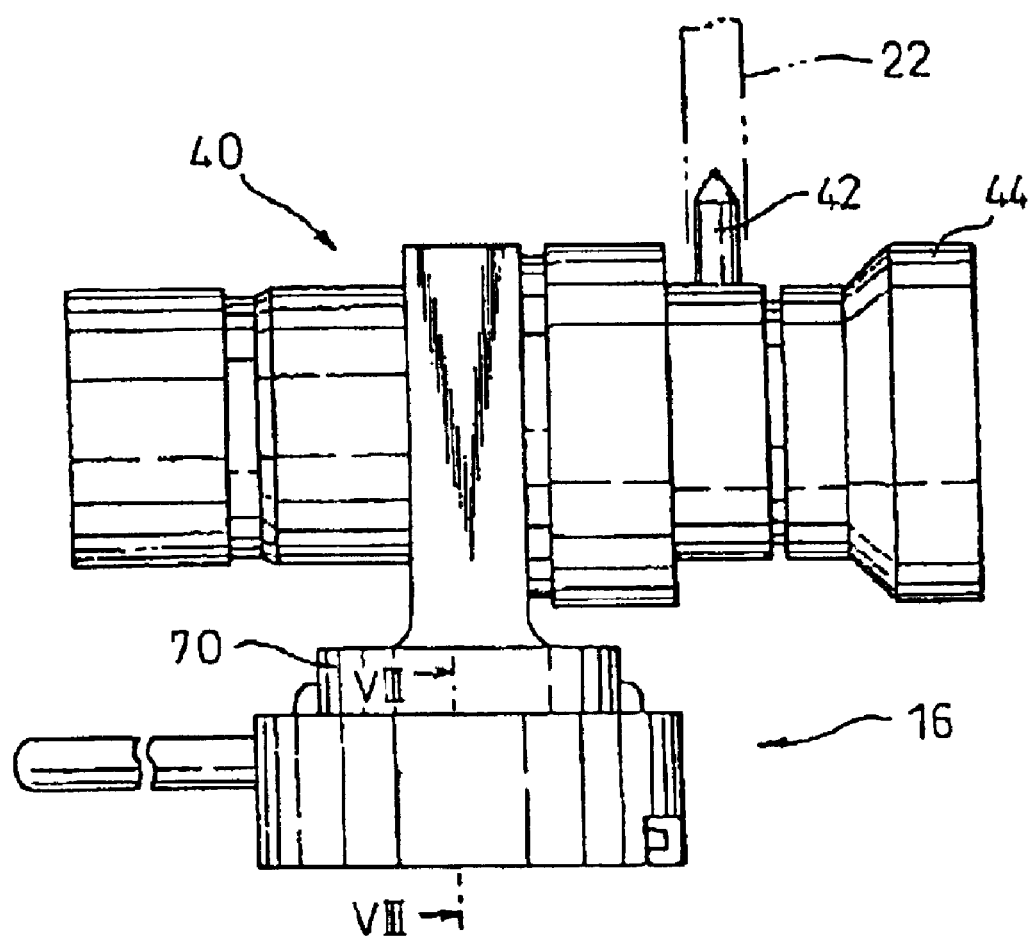
FIG. 1 is a side view of a pressure regulating valve with a coupler according to the invention.

With reference to the drawings, a preferred embodiment of the invention will be described below.

Referring to FIGS. 11A and 11b, a respiratory gas supplying apparatus 10 according to a preferred embodiment of the invention has an oxygen cylinder 12 as a respiratory gas source which is filled with a respiratory gas, for example an oxygen enhanced gas. The oxygen cylinder 12 has a shut-off valve 18. The oxygen cylinder 12 is adapted to be removably mounted to a cart 14. In particular, the oxygen cylinder is adapted to be accommodated in a housing 26 as an accommodating portion which is inclinably mounted to a frame 14a of the cart 14. A flow regulating valve 40 or a demand regulator 120 is mounted to the frame 14a of the cart 14. The flow regulating valve 40 or the demand regulator 120 is connected to the shut-off valve 18 of the oxygen cylinder 12 through a coupler 16 when the oxygen cylinder 12 is accommodated in the housing 26 of the cart 14. The flow regulator is connected to a nasal cannula 24 through a conduit 22 so that the respiratory gas filled in the oxygen cylinder 12 is supplied into a nasal passage of a user (not shown) through the shut-off valve 18, the flow regulating valve or the demand regulator 120, the conduit 22 and the nasal cannula 24.

Referring to FIGS. 12A and 12B, the housing 26 is inclined to one side of the cart 14, as shown in FIG. 12B, to remove the oxygen cylinder 12 from the housing 26 as the accommodating portion of the cart 14. The housing 26 is inclined by pulling with a handle 28 which is rotationally attached to a side wall 26a of the hosing 26 by a hinge member 28 so that the oxygen cylinder 12 can be put in, or removed from, the cart 14.

Referring to FIGS. 1–10, a preferred embodiment of the shut-off valve 18 and the coupler 16, which is connected to the shut-off valve 18, will be described.

Referring to FIG. 1, the coupler 16 has an integrated flow regulating valve 40. The flow regulating valve 40 has an exit port 42 to which the conduit 22 is connected and a flow adjusting knob 44.

Figure 2:
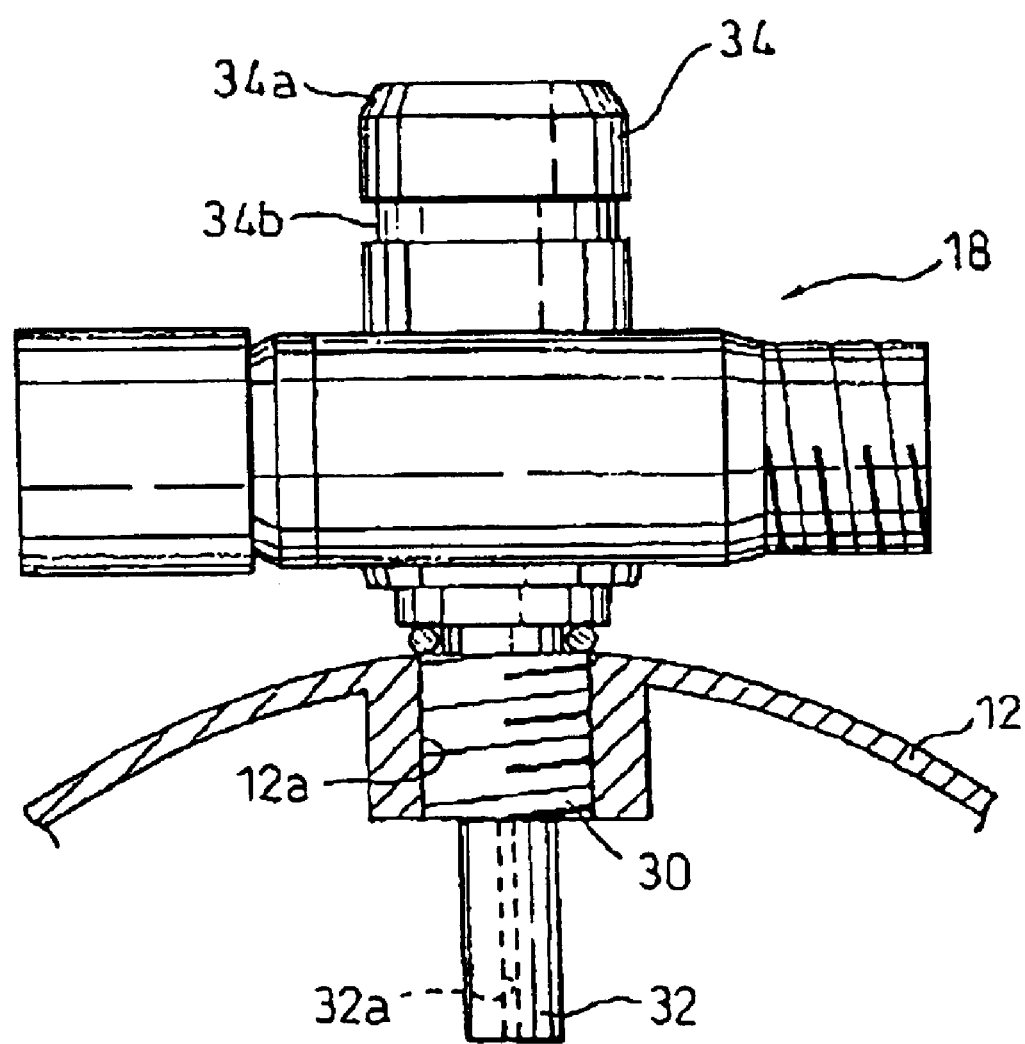
FIG. 2 is a side view of a shut-off valve which is adapted to be mounted on an oxygen cylinder and includes a coupler receiving portion adapted to the coupler shown in FIG. 1.

Referring to FIG. 2, the shut-off valve 18 has, as is well known in the art, a threaded portion 30 which is adapted to be engaged with a threaded portion 12a provided in a top portion of the oxygen cylinder 12. A gas introducing potion 32 is axially downwardly extended from the lower end of the threaded portion 30. The gas introducing portion 32 includes an axially extended inlet port 32a. A coupler mounting portion 34 is provided at the top portion of the shut-off valve 18 to which the coupler 16 is mounted. A tapered portion 34a is defined at the end of the coupler mounting portion 34, and a peripheral groove 34b is defined in the side surface of the coupler mounting portion 34.

Figure 3:
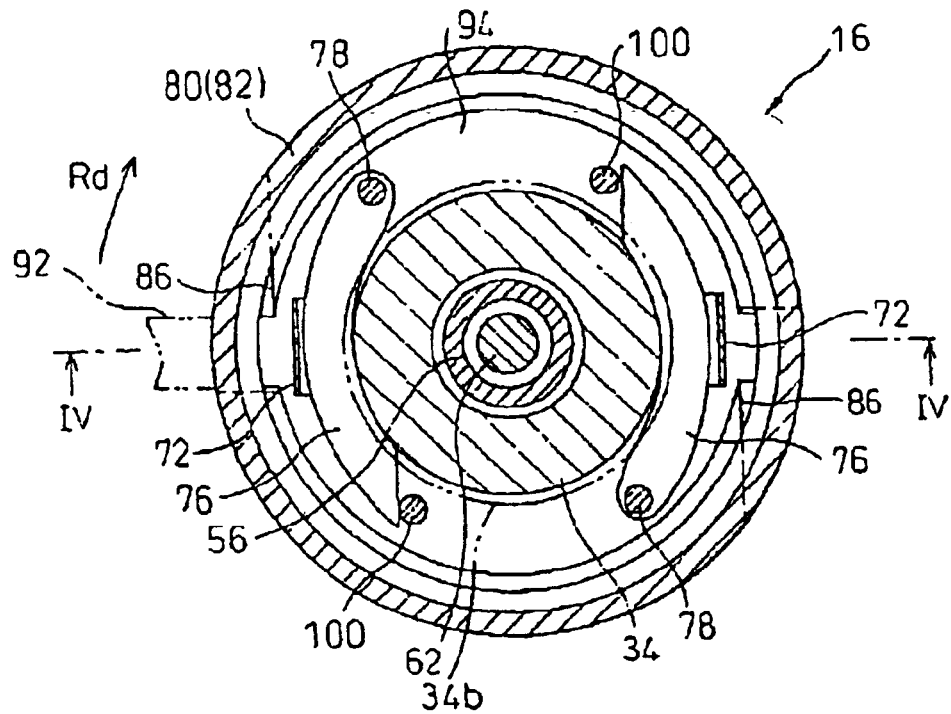
FIG. 3 is a section of the coupler along line III—III in FIG. 4, the coupler of FIG. 1 being mounted to the coupler receiving portion.
Figure 4:
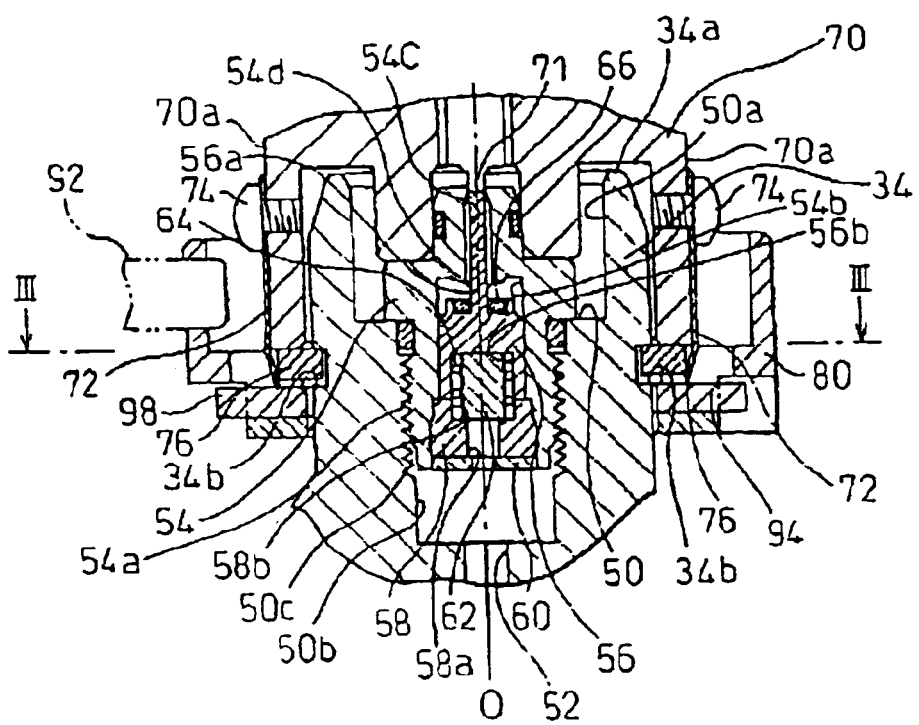
FIG. 4 is a section along line IV—IV in FIG. 3.
Figure 5:
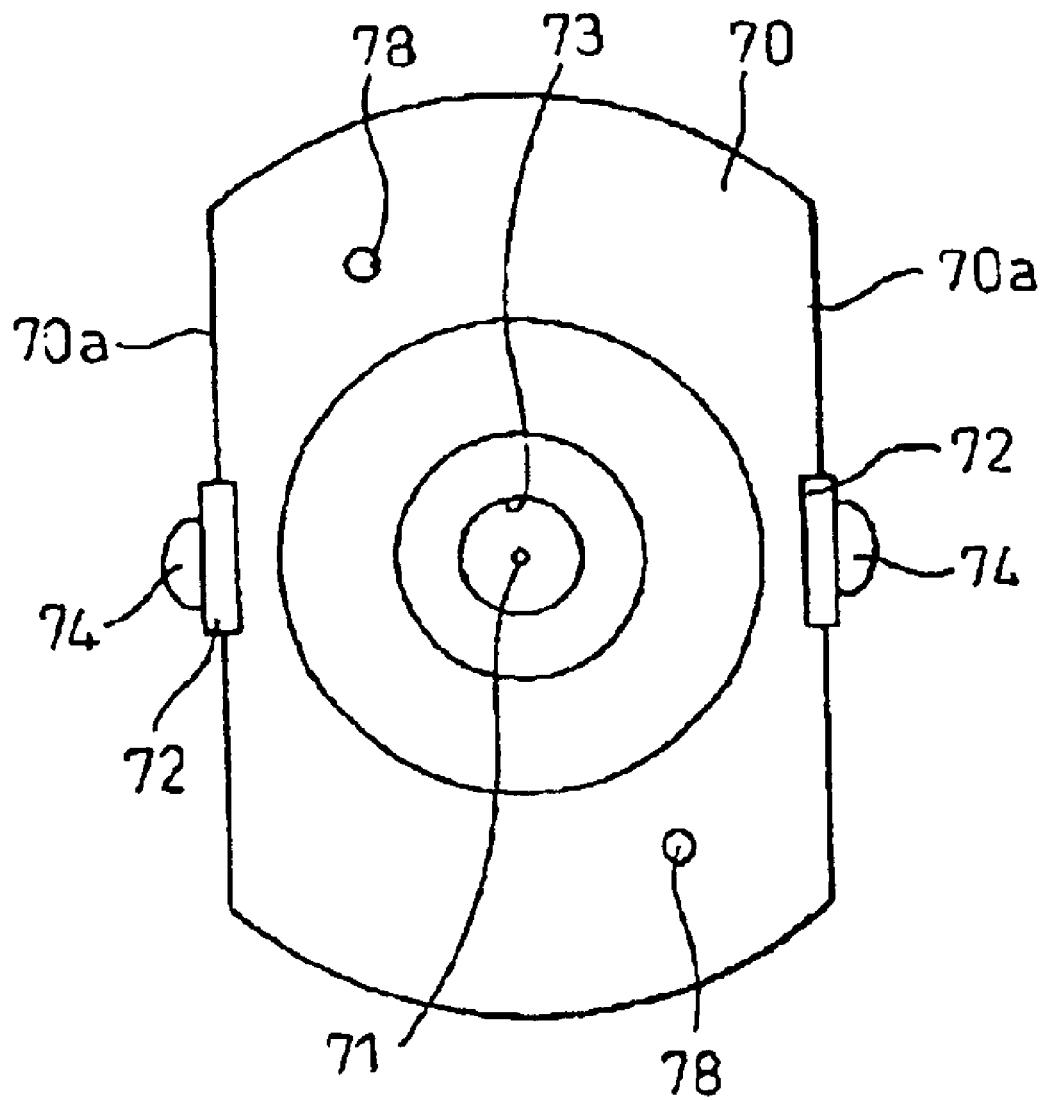
FIG. 5 is a bottom view of the coupler of FIG. 1.

FIGS. 3 and 4 are partial sections of the shut-off valve 18 adjacent the coupler mounting portion 34 with the coupler 16 being coupled. The coupler mounting portion 34 defines a recess 50 which is fluidly connected to the inlet port 32a through a passage 52. A valve housing 54 is disposed in the recess 50. The recess 50 has a major diameter portion 50a and a minor diameter portion 50b. The minor diameter portion 50b defines an inner threaded portion 50c. An outer threaded portion 54a, which engages the inner threaded portion 50c, is formed on the lower portion of the valve housing 54. The engagement between the outer threaded portion 54a and the inner threaded portion 50c secures the valve housing 54 to the coupler mounting portion 34.

The valve housing 54 defines a bore 54b and a valve outlet passage 54c which provides an outlet port of the shut-off valve 18. A piston 56 is axially and slidably provided in the bore 54b. An opening of the bore 54b of the valve housing 54, opposite to the valve outlet passage 54c, is closed by a closure member 58 having a valve inlet passage 58a. The closure member is secured to the valve housing 54 by a snap ring 60. The closure member 58 has a recess 58b fluidly connected to the valve inlet passage 58a. A cylindrical support 62 is disposed in the recess 58b.

The piston 56 has an axially extending piston rod 56a and a recess 56b formed at the end portion opposite to the piston rod 56a. The piston rod 56a has an outer diameter smaller than the inner diameter of the valve outlet passage 54c of the valve housing 54 and extends into the valve outlet passage 54c. A coil spring 64 is provided about the support 62 for biasing the piston 56 away from the closure member 58.

An annular valve seat 54d is defined in the inner surface of the bore 54b of the valve housing 54 around the valve outlet passage 54c. The valve seat 54d extends into the bore 54b. An O-ring 66 is mounted, as a valve body, to a surface of the piston 56 opposing the valve seat 54d. A coil spring urges the piston 56 so that the O-ring 66 moves to a closed position and abuts the valve seat 54d to close the shut-off valve 18. FIG. 4 shows an open position where the O-ring 66 is away from the valve seat 54d.

The coupler 16 comprises a coupler body 70 in the form of a column, which has a section in the form of a circle cut by a pair of parallel chords, a central opening 73 defined in the bottom surface of the coupler body 70 defining an inlet port of the flow regulating valve 40, a protrusion 71, provide coaxially with the central opening 73 to extend from the bottom surface of the coupler body 70, for abutting the piston rod 56a, when the coupler 16 is mounted to the coupler mounting portion 34, to move the piston 56 to the open position against the biasing force of the coil spring 64. The coupler 16 further comprises a pair of engaging claws 76 mounted to the bottom surface of the coupler body 70 and a cover member 60 for enclosing the lower portion of the coupler body 70 and the engaging claws 76. The engaging claws 76 are rotatably mounted about a pair of respective pins 78 extending from the bottom surface of the coupler body 70 and radially and inwardly biased by a pair of respective springs 72 in the form of plates. Each of the plate springs 72 is secured to the side surface 70a of the coupler body 70 by a fastener such as a screw thread. The engaging claws 76 engage the tapered portion 34a of the coupler mounting portion 34 and radially and outwardly rotate when the coupler 16 is mounted to the shut-off valve 18. When the coupler 16 is completely mounted to the shut-off valve 18, the engaging claws 76 fit into the peripheral groove 34b of the coupler mounting portion to prevent the detachment of the coupler 16 from the shut-off valve 18.

Figure 6:
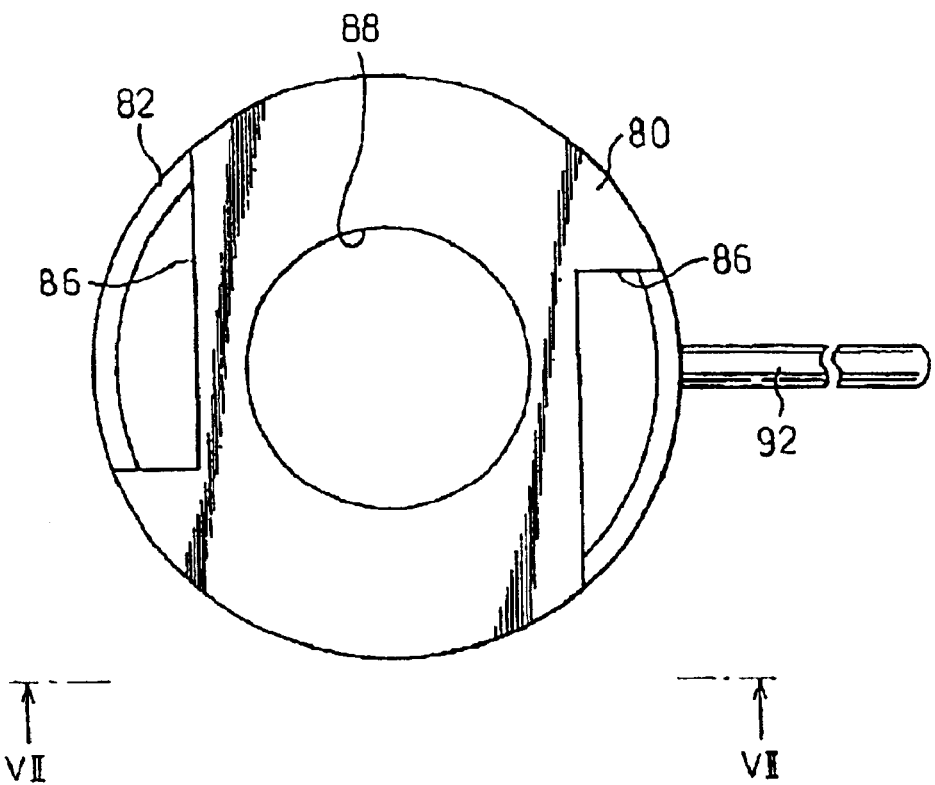
FIG. 6 is a bottom view of a cover member of the coupler of FIG. 1.
Figure 7:
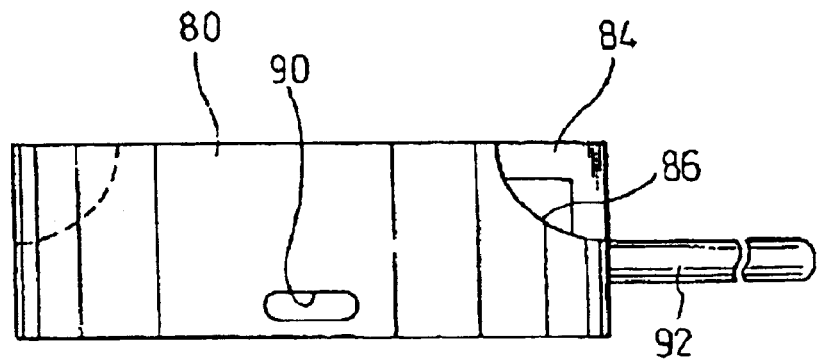
FIG. 7 is a section of the cover member along line VII—VII in FIG. 6.
Figure 8:
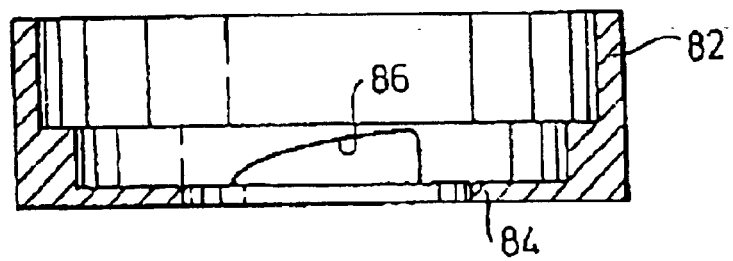
FIG. 8 is a section of the cover member of FIG. 6.
Figure 9:
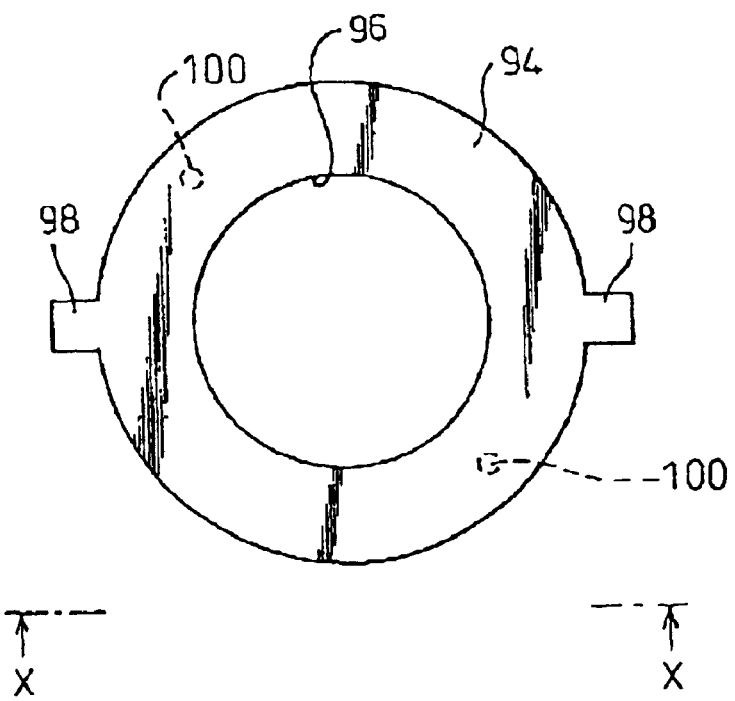
FIG. 9 is a plan view of a plate of the coupler of FIG. 1.
Figure 10:
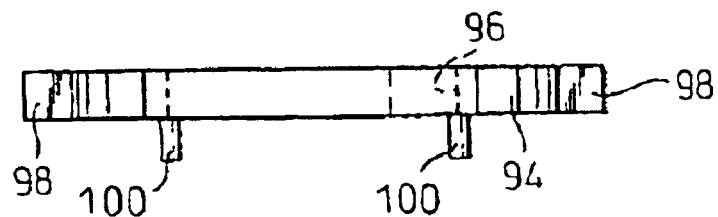
FIG. 10 is a side view of the plate of FIG. 9.

The cover member is as formed, as shown in FIGS. 6–8, into a cup shape having a side wall 82 and a bottom wall 84. A pair of cut-out portion 86 are defined between the side wall 82 and the bottom wall 84. The side wall defines slots 90 for the passage of fasteners such as screw threads (not shown) for rotationally attaching the cover member 80 to the coupler body 70. The bottom wall 84 defines a central opening 88 for passage of the coupler mounting portion 34. Further, a radially extending release lever 92 is attached to the side wall 82 of the cover member 80.

When the coupler 16 is assembled, a plate 94 is disposed between the coupler body 70 and the cover member 80. The plate 94 is an annular member having a central opening 96 and a pair of diametrically opposed tabs 98. A pair of release pins 100 are provided on one end-face of the plate 94. When the coupler 16 is assembled, the tabs 98 extend outwardly through the pair of cut-out portions 86, and the pair of release pins 100 engage the corresponding engaging claws 76.

The operational function of the coupler 16 of this embodiment will be described below.

When the coupler 16 is mounted to the coupler mounting portion 34 of the shut-off valve 18, as shown in FIG. 4, by axially downwardly moving the coupler 16 and the shut-off valve 18 so that the coupler mounting portion 34 passes through the central openings 88 and 96 of the cover member 80 and the plate 94 of the coupler 16, the pair of engaging claws 76 engage the tapered portion 34a of the coupler mounting portion 34 to radially outwardly move away from each other so that the passage of the coupler mounting portion 34 is allowed. The further movement of the coupler 16 in the axial direction, the engaging claws 76 fit into the peripheral groove 34b. The engagement between the claws 76 and the groove 34b axially secures the coupler 16 to the coupler mounting portion 34 of the shut-off valve 18.

When the coupler 16 is detached from the shut-off valve 18 for the replacement of the oxygen cylinder 12, the release lever 92 is used for rotating the cover member 80 in the direction of arrow Rd in FIG. 3. This rotates the plate 94 in the direction of the arrow Rd through the engagement between the cut-out portion 86 of the cover 90 and the tabs 98 of the plate 94. This further rotates the release pins 100 in the direction of the arrows Rd to engage with the claws 76 so that the engaging claws 76 move radially outwardly away from each other. This allows the axial movement of the coupler 16. Thus, the release lever 92, the cover member 80, the plate 94 and the release pins 100 provide a mechanism for releasing the coupler 16.

Figure 13:
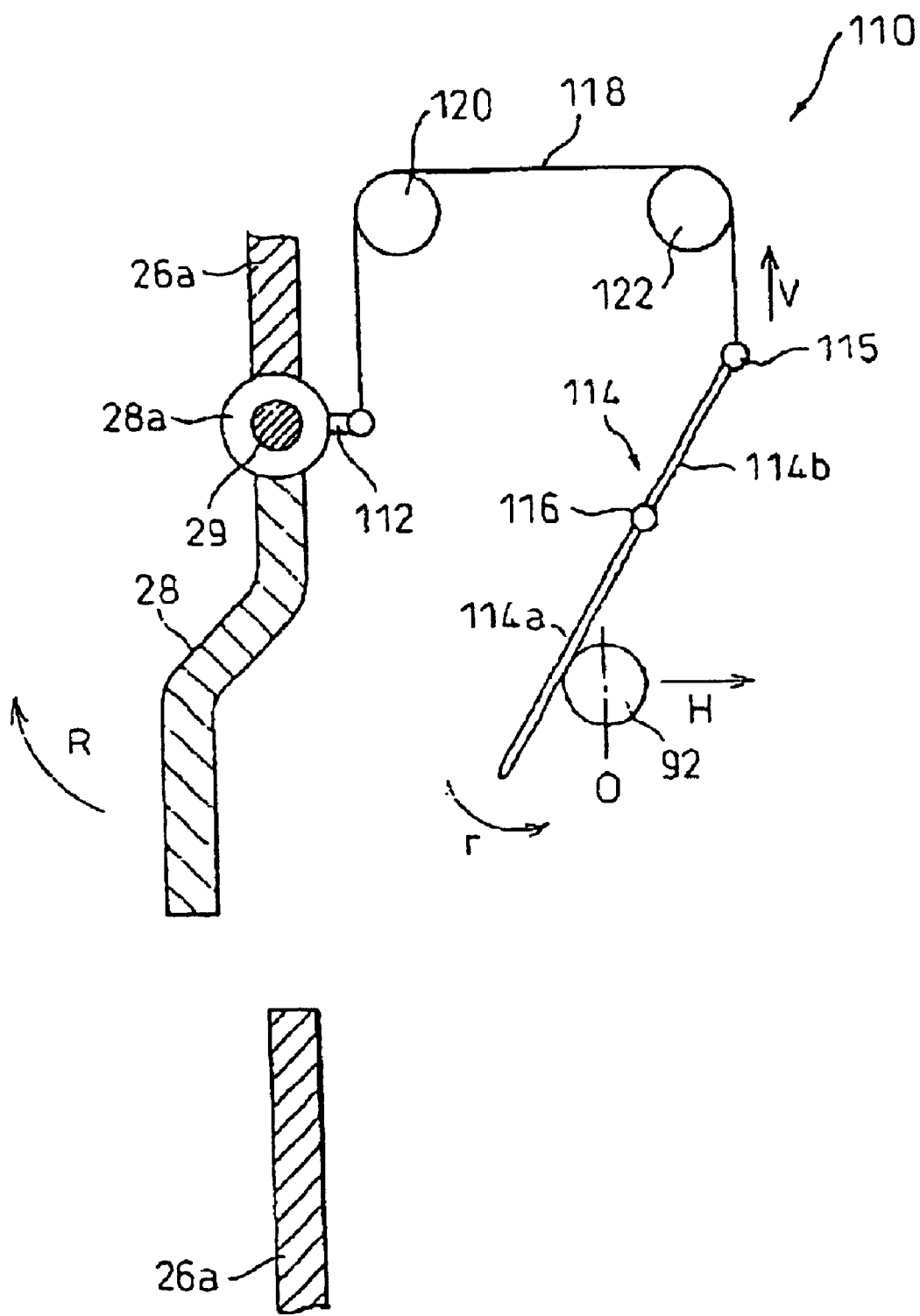
FIG. 13 is a schematic diagram of a linkage mechanism for automatically detaching the coupler from the shut-off valve.

The respiratory gas supplying apparatus 10 according to this embodiment includes a linkage mechanism 110 for automatically detaching the coupler 16 from the coupler mounting portion 34 of the shut-off valve 18 by rotating the cover member 80 of the coupler 16 when the handle 28 is operated for the removing the oxygen cylinder 12 from the cart 14. Referring to FIG. 13, the linkage mechanism 110 includes a lever 114 which is rotatable about a horizontal shaft 116 provided to the inner surface of the cart 14. The lever 114 has a pair of arms 114a and 114b lineally extending in the opposite directions about the shaft 116, one 114a of the arms engaging with the release lever 92. A wire 118 extends within the cart 14 through a plurality of guide pulleys 120 and 122 provided in the cart 14. One end of the wire is connected to an end 115 of the arm 114b of the lever 114, the other end of the wire is connected to a protrusion 112 provided on a hinge portion 28b of the handle 28.

When a user pulls the handle 28 in the direction of arrow R in FIG. 13 for removing the oxygen cylinder 12 from the cart 14, the hinge portion 28a of the handle 29 rotates in the direction of arrow R about a hinge pin 29. This results in the wire 118 pulled by the protrusion 112 to lift the end 115 of the lever 114 in the direction of arrow V. This rotates the lever 114, as shown by arrow r, about the shaft 116 so that the release lever 92 is horizontally rotates as shown by arrow H about an axis O by the arm 114a. Thus, the engaging claws 76 rotate radially outwardly away from each other to disengage the claws 76 from the groove 34b of the coupler mounting portion 34. When the oxygen cylinder 12 is replaced due to the reduction of the internal pressure of the cylinder 12 to a predetermined pressure level, the internal pressure is usually still higher than the atmospheric pressure. Therefore, the coupler 16 is automatically detached from the coupler mounting portion 34 by the pressure remained in the oxygen cylinder 12 when the engaging claws 76 are disengaged from grooves 34b of the coupler mounting portion 34.

In the above-described embodiment, the flow regulating valve 40, for regulating the flow rate of the respiratory gas for the nasal cannula 24 to a predetermined volume, is incorporated with the coupler 16. The invention is not, however, limited to this configuration And, instead of the flow regulating valve 40, a demand regulator, for supplying the respiratory gas to the nasal cannula 24 in synchronism with the breathing of a user, may be used.

Figure 14:
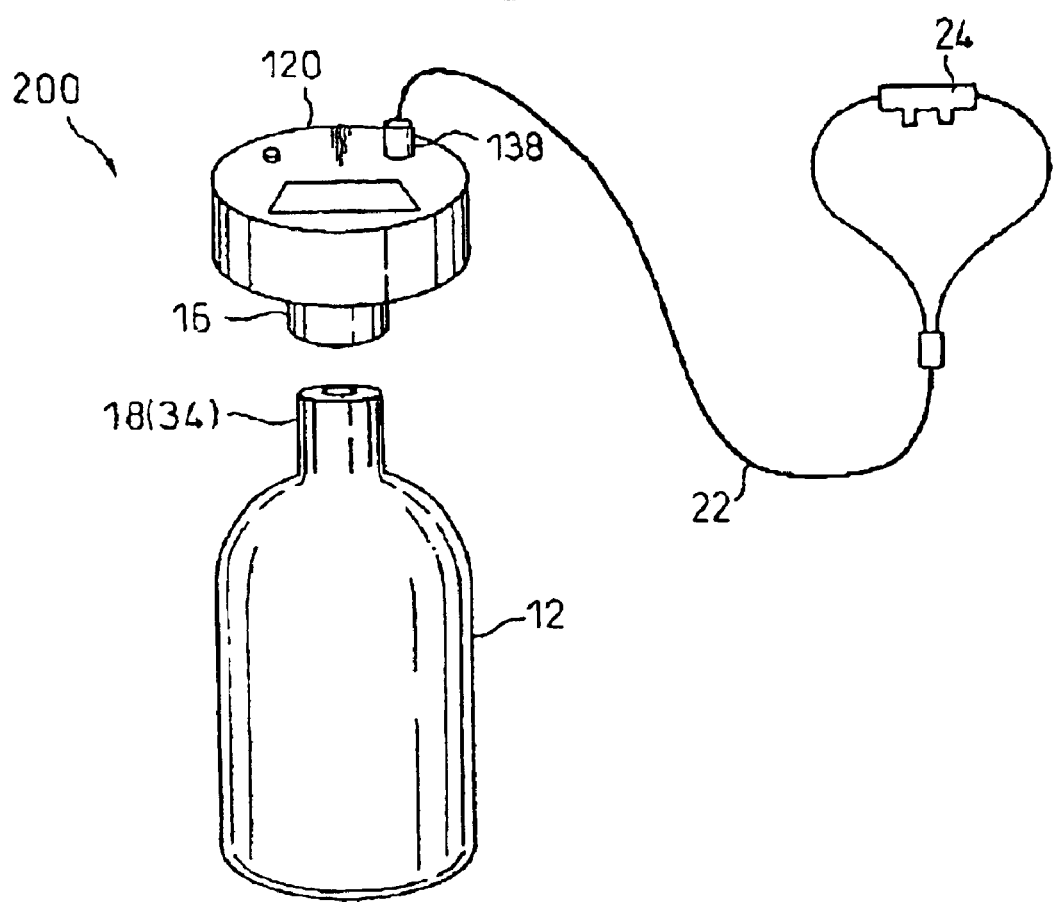
FIG. 14 shows another embodiment of the respiratory gas supplying apparatus according to the invention.

Referring to FIG. 14, a respiratory gas supplying apparatus 200 according to another embodiment has a demand regulator 120 integrated with the coupler 16 so that it is mounted to the shut-off valve 18 of the oxygen cylinder 12 through the coupler 16.

The demand regulator 120 includes an inlet port 121a which is fluidly connected to the outlet port 54c of the shut-off valve 18, when it is attached to the shut-off valve 18, and an outlet port 138 for the connection with the conduit 22. A pressure regulating valve 124 disposed downstream of the shut-off valve 18 as pressure regulating means, a variable orifice 126 disposed downstream of the pressure regulating valve as flow regulating means and supply controlling unit 130 disposed downstream of the variable orifice 126 are provided in a passage 121 between the inlet and outlet ports 121a and 138. The supply control unit 130 includes a solenoid operated valve 136 for fluidly connecting and disconnecting between the inlet port 121a and the outlet port 138, an inspiration sensor 132 for detecting the inspiration of the user or the patient and a solenoid driver circuit 134 for energizing the solenoid to open the solenoid operated valve 136 when the inspiration of the patient is sensed.

The operation of this embodiment will be described below.

Mounting the coupler 16 to the coupler mounting portion 34 of the shut-off valve 18 fluidly connects the passage 121 of the demand regulator 120 to the outlet port 54c of the shut-off valve 18. Under this condition, at the initiation of the inspiration of the user, after the nasal cannula 24 is attached to the use's nose, the inspiration sensor 132 detects the user's inspiration. Thus, the solenoid driver 134 energizes the solenoid 136a so that the solenoid operated valve 136 opens only at the inspiration phases during which the user aspirates. This results in the respiratory gas being supplied to the user only at the inspiration phases.

In addition to the above-described configuration, the respiratory gas supplying apparatus 200 may include a solenoid operated valve 18 as the shut-off valve of the oxygen cylinder 12. In this case, the demand regulator 120 includes a solenoid driver circuit 128 for energizing and de-energizing a solenoid 18a to open and close the solenoid operated valve 18, an electric power source device 140 for the solenoid driver circuit 128 and a switch 141 for the electric power source device 140. This configuration allows the shut-off valve 18 to open by turning the switch 141 on after the demand regulator 120 is mounted to the shut-off valve 12 through the coupler 16.

Further, a pressure sensor 122 may be provided in the passage 121 upstream of the pressure regulating valve 124. In this case, a power source of the demand regulator 120, in particular the electric power source device 140 for the solenoid 136a of the solenoid operated valve 136 can be automatically activated when the pressure in the passage 121 increases to a predetermined high pressure level. Further, a display device 144 may be provided for indicating abnormal pressure in which, for example, the pressure in the passage 121 does not increase to the predetermined high pressure level or the pressure decreases to a predetermined low pressure level.

Figure 15:
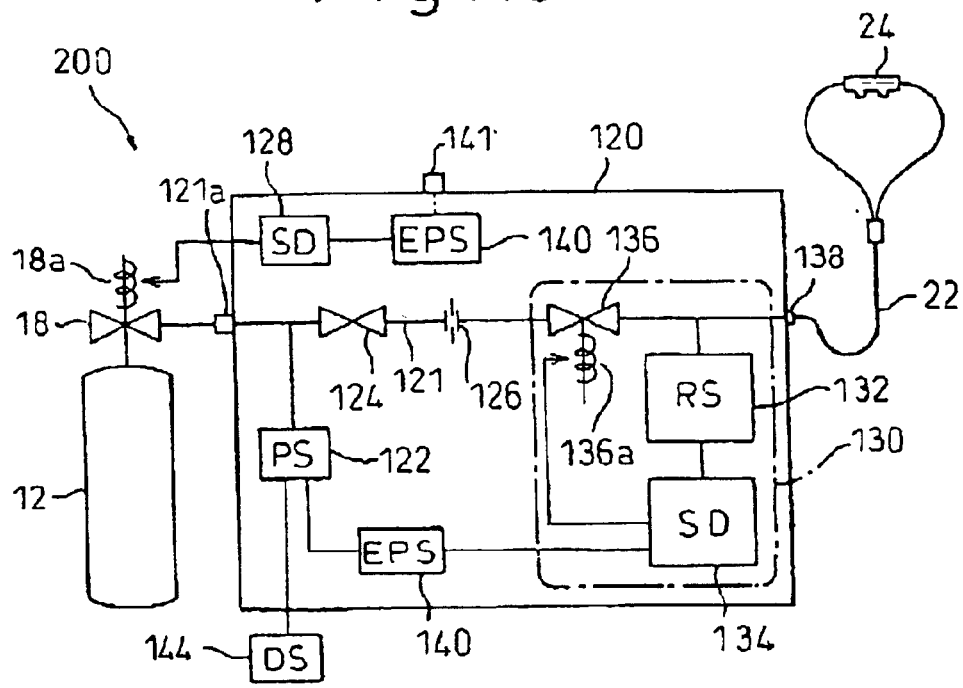
FIG. 15 is a block diagram of the demand regulator according to the embodiment of FIG. 14.
Figure 16:
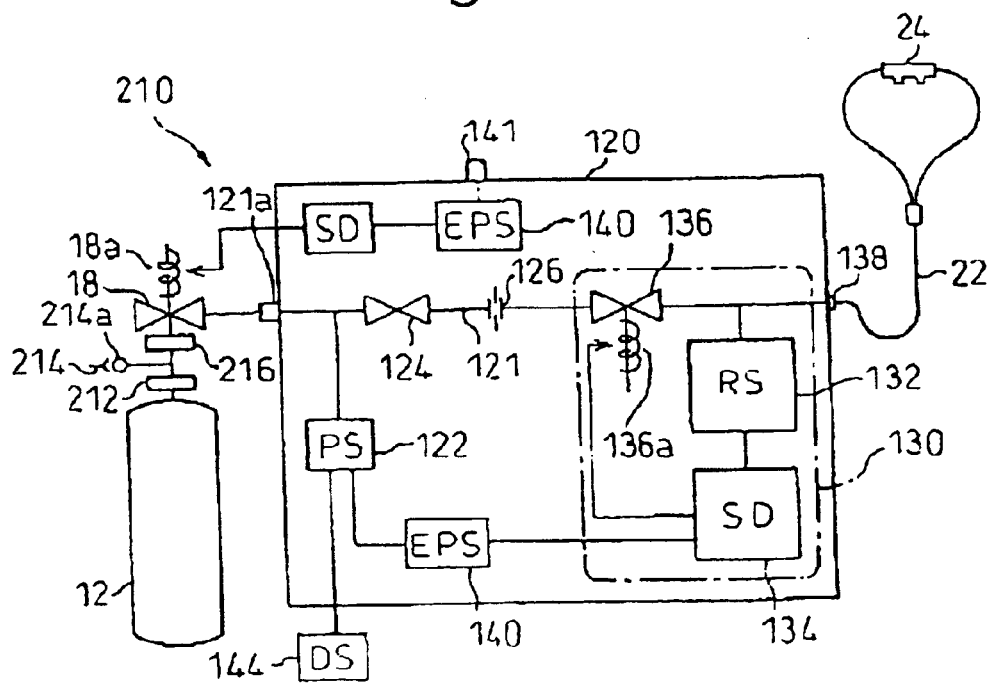
FIG. 16 is a block diagram of the demand regulator according to another embodiment.
Figure 17:
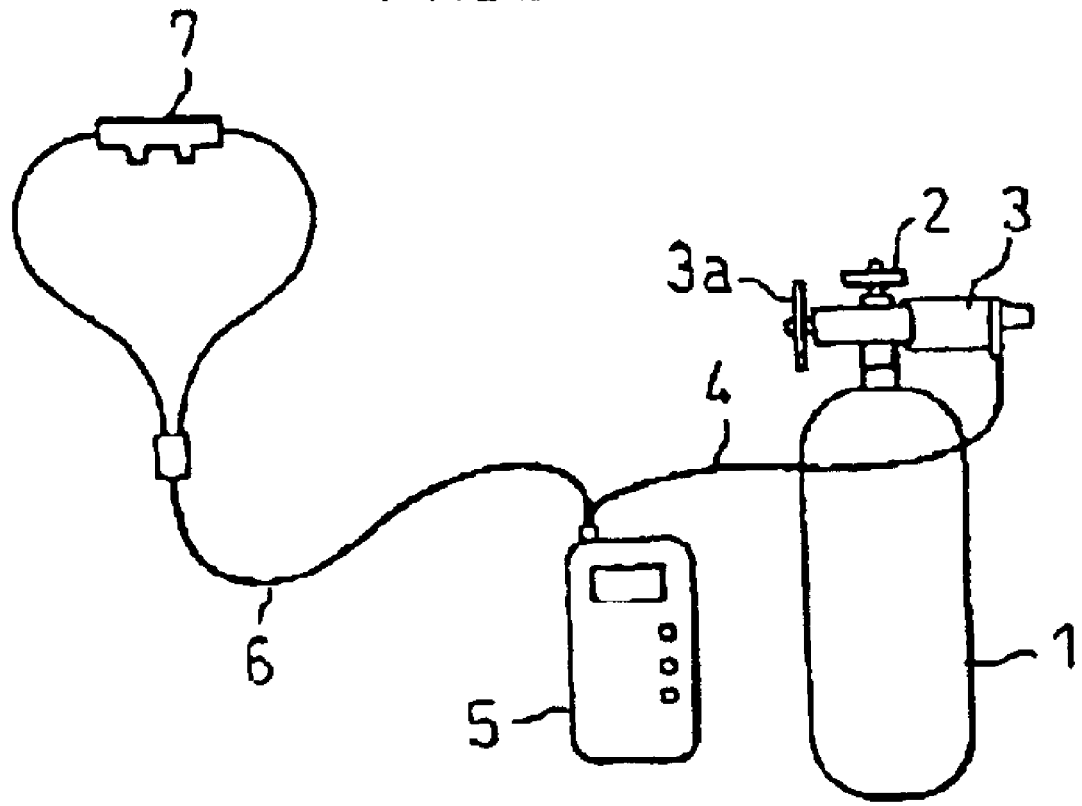
FIG. 17 shows a respiratory gas supplying apparatus of a prior art.

FIG. 16 shows another embodiment of the invention, in which the shut-off valve 18 has a respiratory gas loading port. The respiratory gas supplying apparatus 210 according to the embodiment of FIG. 16 has a is pressure gage 212 for indicating the pressure in the oxygen cylinder 12, a pressure regulating valve 216 provided upstream of the shut-off valve 1B and a respiratory gas loading port 214 provided between the pressure gage 212 and the pressure regulating valve 216. The inspiration loading port has a check valve 214a. The rest of the configuration is the same as the embodiment of FIG. 15 and, in FIG. 16, the elements identical to those in FIG. 15 are indicated by the same reference numbers.

What is claimed is:

1. An apparatus for supplying a respiratory gas to a respiratory airway of a patient, comprising:
    a cylinder filled with a respiratory gas;
    a cart having a frame and a housing, which can incline relative to the frame, for defining an accommodating portion for disposing the cylinder,
    a shut-off valve attached to the cylinder;
    a flow regulating valve adapted to be attached to the shut-off valve;
    a conduit, attached to the flow regulating valve, for directing the respiratory gas to the respiratory airway of the patient;
    a coupler, integrally connected to the flow regulating valve, for coupling the flow regulating valve to the shut-off valve; and
    a linkage mechanism for disconnecting the coupler from the shut-off valve in conjunction with the inclination of the housing.

2. An apparatus according to claim 1
    further comprising a handle, rotatably secured to a wall of the housing, for moving the housing relative to the frame of the cart; and
    the linkage mechanism is connected to the handle.

3. An apparatus according to claim 2, wherein the flow regulating valve has an inlet port for receiving the respiratory gas and an outlet port for discharging the respiratory gas to the conduit;
    the shut-off valve having a coupler mounting portion in the form of a column to which the coupler is mounted;
    the coupler mounting portion including a peripheral groove extending along the outer surface and an outlet port which is adapted to be fluidly connected to
    the coupler including an engaging claw which is adapted to engage the peripheral groove when the coupler is mounted to the coupler mounting portion and a releasing mechanism for disengaging the engaging claw from the peripheral groove when the coupler is detached from the coupler mounting portion; and
    the linkage mechanism engages the releasing mechanism when the cylinder is mounted to the cart.

4. An apparatus for supplying a respiratory gas to a respiratory airway of a patient, comprising:
    a cylinder filled with a respiratory gas;
    a cart having a frame and a housing, which can incline relative to the frame, for defining an accommodating portion for disposing the cylinder;
    a shut-off valve attached to the cylinder;
    a demand regulator adapted to be attached to the shut-off valve;
    a conduit, attached to the demand regulator, for directing the respiratory gas to the respiratory airway of the patient;
    a coupler, integrally connected to the demand regulator, for coupling the demand regulator to the shut-off valve; and
    a linkage mechanism for disconnecting the coupler from the shut-off valve in conjunction with the inclination of the housing.

5. An apparatus according to claim 4 further comprising
a handle, rotatably secured to a wall of the housing, for moving the housing relative to the frame of the cart; and the linkage mechanism is connected to the handle.

6. An apparatus according to claim 5, wherein the demand regulator has an inlet port for receiving the respiratory gas and an outlet port for discharging the respiratory gas to the conduit;

the shut-off valve having a coupler mounting portion in the form of a column to which the coupler is mounted;

the coupler mounting portion including a peripheral groove extending along the outer surface and an outlet port which is adapted to be fluidly connected to the inlet port of the demand regulator when the coupler is mounted to the coupler mounting portion;

the coupler including an engaging claw which is adapted to engage the peripheral groove when the coupler is mounted to the coupler mounting portion and a releasing mechanism for disengaging the engaging claw from the peripheral groove when the coupler is detached from the coupler mounting portion; and the linkage mechanism engages the releasing mechanism when the cylinder is mounted to the cart.

7. An apparatus according to claim 6, wherein the demand regulator comprises a passage extending between the inlet port and the outlet port, pressure regulating means provided in the passage, a flow regulating means provided downstream of the pressure regulating means and a supply controlling unit, provided downstream of the flow regulating means, for fluidly connecting the outlet port to the inlet port when the patient is in an inspiration phase to supply the respiratory gas to the patient.

8. An apparatus according to claim 7, wherein the supply controlling unit comprises an inspiration sensor for detecting inspirations of the patient, a solenoid operated valve for fluidly connecting and disconnecting the inlet port and the outlet port and a solenoid driver circuit for opening the solenoid operated valve when the inspiration sensor detects the inspiration of the user.

9. An apparatus according to claim 8 further comprising an electric power source device for driving the solenoid of the solenoid operated valve;

the demand regulator further comprising a pressure sensor for detecting the pressure in the passage, the demand regulator activating the electric power source when the pressure in the passage increases to a predetermined high level and deactivating the electric power source device when the pressure in the passage decrease to the predetermined low level.

10. An apparatus according to claim 8, wherein the shut-off valve attach to the cylinder comprises a solenoid operated valve; and the demand regulator comprising a solenoid driver circuit for driving the solenoid of the solenoid operated valve, an electric power source device and a switch for opening and closing the shut-off valve through the solenoid driver circuit.

11. An apparatus for supplying a respiratory gas to a respiratory airway of a patient, comprising:

a cylinder filled with a respiratory gas;

a cart having a frame and a housing, which can incline relative to the frame, for defining an accommodating portion for disposing the cylinder;

a shut-off valve attached to the cylinder;

a demand regulator adapted to be attached to the shut-off valve;

a conduit, attached to the demand regulator, for directing the respiratory gas to the respiratory airway of the patient; and a coupler, integrally connected to the demand regulator, for coupling the demand regulator to the shut-off valve; and a linkage mechanism for disconnecting the coupler from the shut-off valve in conjunction with the inclination of the housing.

12. An apparatus according to claim 11, wherein the demand regulator has an inlet port for receiving the respiratory gas and an outlet port for discharging the respiratory gas to the conduit;

the shut-off valve having a coupler mounting portion in the form of a column to which the coupler is mounted;

the coupler mounting portion including a peripheral groove extending along the outer surface and an outlet port which is adapted to be fluidly connected to the inlet port of the demand regulator when the coupler is mounted to the coupler mounting portion; and the coupler including an engaging claw which is adapted to engage the peripheral groove when the coupler is mounted to the coupler mounting portion and a releasing mechanism for disengaging the engaging claw from the peripheral groove when the coupler is detached from the coupler mounting portion.

13. An apparatus according to claim 12, wherein the demand regulator comprises a passage extending between the inlet port and the outlet port, pressure regulating means provided in the passage, a flow regulating means provided downstream of the pressure regulating means and a supply controlling unit, provided downstream of the flow regulating means, for fluidly connecting the outlet port to the inlet port when the patient is in inspiration phase to supply the respiratory gas to the patient.

14. An apparatus according to claim 13, wherein the supply controlling unit comprises an inspiration sensor for detecting inspirations of the patient, a solenoid operated valve for fluidly connecting and disconnecting the inlet port and the outlet port and a solenoid driver circuit for opening the solenoid operated valve when the inspiration sensor detects the inspiration of the user.

15. An apparatus according to claim 14 further comprising an electric power source device for driving the solenoid of the solenoid operated valve;

the demand regulator further comprising a pressure sensor for detecting the pressure in the passage, the demand regulator activating the electric power source when the pressure in the passage increases to a predetermined high level and deactivating the electric power source device when the pressure in the passage decrease to the predetermined low level.

16. An apparatus according to claim 14, wherein the shut-off valve attached to the cylinder comprises a solenoid operated valve; and the demand regulator comprises a solenoid driver circuit for driving the solenoid of the solenoid operated valve, an electric power source device and a switch for opening and closing the shut-off valve through the solenoid driver circuit.

* * * * *